United States Patent [19]

Wilcox

[11] 4,052,194
[45] Oct. 4, 1977

[54] OXIME ABSCISSION AGENTS

[76] Inventor: Merrill Wilcox, 2911 NW. 30th Terrace, Gainesville, Fla. 32601

[21] Appl. No.: 618,880

[22] Filed: Sept. 16, 1975

Related U.S. Application Data

[63] Continuation of Ser. No. 436,297, Jan. 24, 1974, abandoned, which is a continuation-in-part of Ser. No. 275,657, July 27, 1972, abandoned.

[51] Int. Cl.$^2$ .............................................. A01N 9/20
[52] U.S. Cl. ......................................... 71/121; 71/88; 71/94; 71/98; 71/106; 71/115; 260/290 R; 260/345.1; 260/346.11; 260/347.2; 260/347.7; 260/429.9; 260/439 R; 260/438.1; 260/455 B; 260/463; 260/515 A; 260/566 A; 260/566 AC; 260/566 AE
[58] Field of Search ............................. 71/121, 98, 97

[56] References Cited

U.S. PATENT DOCUMENTS

| | | | |
|---|---|---|---|
| 2,535,877 | 12/1950 | Stewart | 71/77 |
| 3,001,908 | 9/1961 | Harrison | 424/283 |
| 3,515,536 | 6/1970 | Hill et al. | 71/77 |
| 3,592,920 | 7/1971 | Gutman et al. | 71/121 |

FOREIGN PATENT DOCUMENTS

| | | | |
|---|---|---|---|
| 399,823 | 4/1966 | Switzerland | 71/121 |

OTHER PUBLICATIONS

Grundmann, "Dicyan bis (N-oxide)", (1963), CA59, p. 6251, (1963).
Hileman, Jr. et al., "The Oximation of Biacetyl", (1965), CA62, p. 16008, (1965).

Primary Examiner—Glennon H. Hollrah
Attorney, Agent, or Firm—Harry Falber

[57] ABSTRACT

A method of aiding in harvesting fruit wherein abscission is induced by application to the fruit bearing plant of an effective amount of a compound of the formula

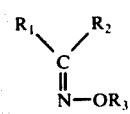

(I)

or a salt thereof, wherein $R_1$ is hydrogen, halogen, alkyl, alkenyl, phenylalkyl or furyl, $R_2$ is hydrogen, alkyl, cycloalkyl, phenyl, carboxy, carbalkoxy, carbanilido, heterocyclic or a group

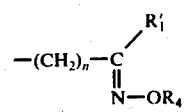

in which $R_1'$ has the same meanings as $R_1$, $n$ is an integer from 0 to 3, and wherein $R_1$ and $R_2$ when taken together form a $C_3$–$C_{12}$ ring and $R_3$ and $R_4$ represent hydrogen, alkyl, alkenyl, alkylcarbonyl, phenylcarbonyl, N-alkylcarbamoyl, N-alkylthiocarbamoyl, N,N-dialkylcarbamoyl, phenylcarbamoyl, phenylalkyl, alkoxycarbonyl, phenoxycarbonyl, phenylalkoxycarbonyl, alkylthiocarbonyl, phenylthiocarbonyl, α-furyl and tetrahydropyranyl.

3 Claims, No Drawings

OXIME ABSCISSION AGENTS

RELATED APPLICATIONS

This is a continuation of application Ser. No. 436,297, filed on Jan. 24, 1974, now abandoned, which, in turn, is a continuation-in-part of application Ser. No. 275,657, filed July 27, 1972, now abandoned.

BACKGROUND OF THE INVENTION

The ability of plants to slough off organs by an active separation of cells is distinctive to higher green plants. Plant physiologists describe this process as abscission.

As our agricultural production has become more intensified, the use of mechanical harvesters has become more and more important in agricultural production. Their use helps to keep the unit cost of production down to a reasonable level. Where hand labor is still used in harvesting crops, any practice that can help to increase the productivity of a man per unit of time, would be an important agricultural contribution.

This invention relates to the use of certain chemicals which have a positive and beneficial effect on the abscission process. They facilitate and make the harvesting of crops easier. This is a new and unique discovery and is highly important in the agricultural sector. To harvest fruit, as given in the examples above, whether it is done by hand or mechanically, a given amount of force (energy) must be applied by hand or mechanically to the fruit, or portion of the plant to be harvested, in order to force it to abscise, or come loose from the rest of the plant. It is recognized that when a great deal of force must be applied during the harvesting operation: (1) the amount of fruit harvested in a given time is reduced as compared with fruit which is more easily loosened and taken from the plant, (2) the fruit may be damaged or reduced in quality grade because of the amount of force which must be applied, (3) some fruit becomes unmarketable because of excessive damage to the fruit, and (4) the plant itself may be damaged and in the case of perennial plants such as vines or trees, this is highly undesirable; also, in the case of annual plants where multiple harvests are to be made, damage at the first or earlier pickings is undesirable and should be avoided.

Chemicals used to assist in loosening the fruit for the harvesting operation are sometimes called, in general terms, harvesting aid chemicals or fruit loosening chemicals. If the amount of force needed to separate a fruit from the rest of the plant can be reduced through the use of a chemical, this would be a significant contribution to agriculture and would be useful to farmers and growers. Such a chemical would allow pickers to pick the fruit easily and more quickly. In the case where mechanical harvesters are used, the amount of force which would have to be applied by the mechanical harvester could be reduced. More fruit per tree (per vine, or unit or row) could be harvested more easily and uniformly. Less damage to the fruit itself and to the rest of the plant would result if a chemical loosening agent effectively reduced the required harvest force. The quality of the fruit would increase because of less damage and possibly the yield per tree (per acre, or per unit of measure) would increase because of a more uniform and complete harvest. The compounds of this invention do help to loosen the fruit which is to be harvested while at the same time, they do not significantly damage the rest of the plant.

Various abscission agents have already been suggested, but these are frequently unsatisfactory on account of undesirable side-effects. An example of these is cycloheximide, which, in spite of an excellent abscission action in the case of the citrus fruits, has a great disadvantage in that it severely damages blossom and unripe fruit on the tree, has a pronounced defoliating action, and gives rise to considerable scarring on ripe fruit.

The process according to the invention comprises the treatment of the fruit-bearing plants or of the fruits themselves with an effective amount of a compound of the general formula I

or with a salt of such a compound.

The symbols in formula I have the following meanings:

$R_1$ is hydrogen, halogen, especially chlorine, a substituted or unsubstituted alkyl radical having 1 to 17 carbon atoms, $C_2$–$C_5$ alkenyl, substituted or unsubstituted phenylalkyl or α-furyl;

$R_2$ is hydrogen, $C_1$–$C_{17}$ substituted and unsubstituted alkyl, $C_3$–$C_6$ cycloalkyl, substituted and unsubstituted phenyl, carboxy, carbalkoxy, carbanilido, a heterocyclic radical such as pyridyl and furyl, or a group

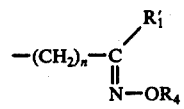

wherein $R_1'$ has the same meanings as $R_1$, $n$ is an integer from 0 to 3.

$R_1$ and $R_2$ taken together form a $C_3$–$C_{12}$ ring, and $R_3$ and $R_4$ each independently represent hydrogen and substituted or unsubstituted radicals chosen from the group consisting of $C_1$–$C_{12}$ alkyl, $C_2$–$C_5$ alkenyl, alkylcarbonyl, phenylcarbonyl, N-alkylcarbamoyl, N-alkylthiocarbamoyl, N,N-dialkylcarbamoyl, phenylcarbamoyl, phenylalkyl, alkoxycarbonyl, phenoxycarbonyl, phenylalkoxycarbonyl, alkylthiocarbonyl, phenylthiocarbonyl, α-furyl and tetrahydropyranyl, $C_1$–$C_6$ alkyl, alkoxy or alkylthio groups are preferred when forming part of substituted $R_1$, $R_1'$, $R_2$, $R_3$ or $R_4$ substituent groups.

The compounds of formula I are therefore oximes and dioximes, the O-substituted derivatives and salts. Substituents on the oxygen atom ($R_3$ and $R_4$) are, as can be seen above, preferably such radicals which are readily split off hydrolytically, aminolytically or metabolically in the plant or in the application agent (spray emulsion) with the formation of the free oxime group ($R_3$=$R_4$=H). Particularly suitable radicals for $R_3$ and $R_4$ are those used in synthetic chemistry as protective-groups of alcohols (acyl radicals, etc.).

Applicable substituents of substituted radicals $R_1$, $R_1'$, $R_2$, $R_3$ and $R_4$ are: halogen, the oxo group, alkoxy, phenoxy, dialkylamino, alkylthio, hydroxy, amino, nitro, N-pyrridylium, trialkylammonio, and the like. As previously indicated, $C_1$–$C_6$ alkyl, alkoxy or alkylthio radicals are preferred for this purpose.

The compounds of formula I can be present as cis- and trans-forms.

Preferred compounds for the described field of applicaton are the dioxime derivatives of formula II

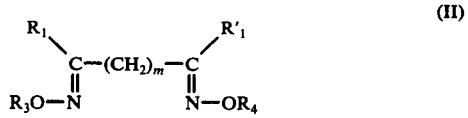

wherein
$R_1$ and $R_1'$ each independently represent hydrogen, chlorine or methyl groups,
$m$ denotes the number 0, 1 or 2, and
$R_3$ and $R_4$ represent hydrogen or unsubstituted or substituted alkylcarbonyl, phenylcarbonyl, alkylcarbamoyl, dialkylcarbamoyl, alkoxycarbonyl, phenoxycarbonyl, alkylthiocarbonyl or phenylthiocarbonyl radicals; the alkyl, alkoxy and alkylthio radicals thereof again preferably containing from 1 to 6 carbon atoms.

Salts of these dioximes are also suitable, both the salts of strong acids, such as the hydrohalides and the sulfates, and, if $R_3$ and/or $R_4$ is hydrogen, the salts of bases, such as the alkali metal salts and alkaline-earth metal salts, as well as the salts of other bivalent and trivalent metals, such as Fe, Cu, Zn, Mn, Co and Al, and also the salts of strong amines, such as ethanolamine and isopropanolamine.

Particularly preferred are glyoxime and derivatives of the glyoxime of formula III

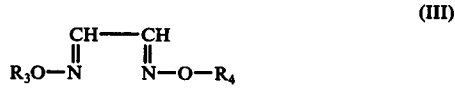

wherein $R_3$ and $R_4$ each independently represent hydrogen, alkylcarbonyl, alkylcarbamoyl and alkoxycarbonyl, each containing $C_1-C_6$ alkyl or alkoxy substituent groups, as well as the above noted salts of glyoxime.

Particular compounds within the scope of the present invention include, for example, O-(2-Chloroethoxycarbonyl)butanone oxime, dichloroglyoxime, dimethylglyoxime, monomethylglyoxime, monochloroglyoxime. Particularly preferred compounds include glyoxime and dichloroglyoxime.

The active substances used according to the invention are in some cases known and are prepared in accordance with conventional techniques. Typical preparation procedures include, for example, the reaction of acetaldehyde and nitric acid and the reaction of resulting glyoxal with hydroxylamine, the electrolysis of nitric acid. See also, Beilstein, Volume 1, page 761 and supplements.

New active substances not hitherto described in the literature are, for example, glyoxime derivatives of the more restricted formula IV

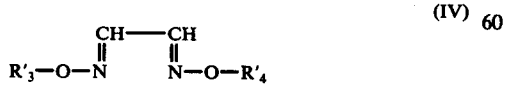

wherein $R_3'$ represents hydrogen, $C_1$ to $C_{14}$ alkyl, $C_3-C_6$ alkenyl, phenylalkyl, N-alkylcarbamoyl, N-alkylthiocarbamoyl, N,N-dialkylcarbamoyl, N-phenylcarbamoyl, alkoxycarbanoyl, phenoxycarbonyl, alkylthiocarbonyl, or tetrahydropyranyl, and $R_4'$ represents $C_1-C_{14}$ alkyl, $C_3-C_6$ alkenyl, phenylalkyl, alkylcarbonyl, phenylcarbonyl, N-alkylcarbamoyl, N-alkylthiocarbamoyl, N,N-dialkylcarbamoyl, N-phenylcarbamoyl, alkoxycarbonyl, phenyloxycarbonyl, alkylthiocarbonyl, or tetrahydropyranyl. In each instance, the substituted alkyl, alkoxy or alkylthio group contains from 1 to 6 carbon atoms.

These compounds are also provided in a known manner by a process in which glyoxime or a salt thereof is treated in a solvent such as acetonitrile, acetone, ether, etc., and optionally in the presence of an acid-binding agent, e.g. triethylamine, with an agent introducing the radical $R_3'$ or $R_4'$. Suitable agents are, for example, acetyl chloride, phenylisocyanate, dimethylcarbamoyl chloride, methylbromide, chloroformic acid ester, chlorothioformic acid ester, benzylbromide, alkylisocyanates, alkylisothiocyanates, etc.

The following examples describe the preparation of some new oxime derivatives of formula I or IV. Further oxime derivatives which can be used as active substance for the process according to the invention are listed in the following tables. The temperatures are expressed in degrees Centigrade.

EXAMPLE 1

Glyoxime-O-monoacetate

1 Part of acetyl chloride is added dropwise at 0° to a solution of 1 part of glyoxime and 2 parts of triethylamine in 5 parts of acetonitrile. After being stirred overnight at room temperature, the reaction mixture is concentrated by evaporation to dryness, taken up in water and extracted with ethyl acetate. The organic phase is dried with magnesium sulphate and concentrated, whereby the product crystallises out as fine, white needles (mp. 124°-6°).

EXAMPLE 2a

Glyoxime-O,O'-bis-phenylcarbamate 0.1 Mole of finely powdered glyoxime is suspended in 100 ml of acetonitrile. After the addition of 0.2 mole of phenylisocyanate, stirring is maintained for ca. 15 hours at 20°. The fine, pasty precipitate is filtered off and dried in Vacuo; yield: 95%, mp. 180° (decomposition).

EXAMPLE 2b

Glyoxime-O,O'-bis-dimethylcarbamate

2 Parts of dimethylcarbamoyl chloride are added dropwise at 30°-35° to a solution of 1 part of glyoxime and 2 parts of triethylamine in 5 parts of acetonitrile. The formed triethylamine-HCl is filtered off and the filtrate concentrated by evaporation. The residue is taken up in ethyl acetate and the solvent evaporated off. The light-coloured, crystalline product decomposes on being dried in vacuo at 60°; mp. 134° (decomposition).

EXAMPLE 3

Glyoxime-O-bis-methyl ether

An excess of methylbromide is introduced into a solution of glyoxime-Na-salt at 0°. After a stirring overnight, the precipitated Na Br is filtered off. From the filtrate there are obtained the desired product, mp. 225°, and a secondary product, mp. 204°.

EXAMPLE 4

Glyoxime-O,O'-bis-ethylthiocarbonate

2 Parts of chlorothioformic acid-S-ethyl ester are added dropwise at 0° to a solution of 1 part of glyoxime and 2 parts of triethylamine in 5 parts of acetonitrile. A gas ($CO_2$) is evolved during the reaction. The reaction mixture is filtered off from triethylamine hydrochloride and the filtrate concentrated in vacuo. The oily decomposable residue has a smell of mercaptan.

EXAMPLE 5

Glyoxime-O,O'-bis-benzyl ether 22 g of glyoxime is dissolved in 200 ml of 2.5N NaOH at room temperature and 1 liter of acetone added to the solution, whereby the glyoxime-di-Na-salt precipitates. This is dissolved in 10 parts of methanol and 2 parts of benzylbromide are added, whereon a slight exothermic reaction occurs. After several hours' stirring, dilution is performed with methylene chloride, the NaBr removed by filtration and, by concentration of the filtrate by evaporation, a white product, mp. 72°, obtained (yield: ca. 65%).

EXAMPLE 6

O,O-bis-tetrahydro-2-pyranylglyoxime

An amount of 13.2 g of glyoxime is suspended in 50.4 g of 3,4-dihydro-2H-pyran. After dilution with 50 ml of absolute tetrahydrofuran, 50 mg of dry HCl-gas is introduced. The mixture is heated at 45° until a solution is formed. This is stirred, without further heating, for 6 hours, and is then poured into 500 ml of saturated soda solution. After extraction of the soda solution three times with ether, and drying and concentration of the organic phases by evaporation, a yellow-brown oil is obtained, which is dried in vacuo at 0.1 mm and 20°; yield: 33.3 g = 86.5% $n_{20}{}^D$: 1.5084.

EXAMPLE 7

O,O'-bis-isobutyroylglyoxime

2 Parts of isobutyroyl chloride are added dropwise at 10° to a solution of 1 part of glyoxime and 2 parts of triethylamine in 5 parts of acetonitrile. Filtration is performed after 2 hours stirring at 20°; the filtrate is concentrated by evaporation, taken up in methylene chloride, and washed with water. The product, mp. 92°, is obtained from the dried organic phase after concentration by evaporation and recrystallisation from ethyl acetate (80% yield).

EXAMPLE 8

Glyoxime-O-mono-N-methylcarbamate

An amount of 0.4 mole of methylisocyanate is slowly added dropwise at 30° to a solution of 35 g of glyoxime in 1 liter of abs. ether. After being stirred overnight at 20°, the reaction mixture is concentrated cold by evaporation to dryness. The residue is taken up in acetonitrile, and insoluble substance removed by filtration (bis-methylcarbamate); concentration by evaporation is then repeated. The dark residue (50 g) decomposes spontaneously on drying in vacuo at 40°; mp. 40° (slow heating up).

EXAMPLE 9

O-Acetyl-O'-N-methyl-carbamoylglyoxime

1 Part of methylisocyanate is added to a solution of 1 part of mono-O-acetylglyoxime (Example 1) in 5 parts of acetronitrile, and stirring carried out for 4 hours at 20°. The precipitated product is filtered off; mp. 138°; yield 90%.

EXAMPLE 10

18.7 g of chloroacetaldoxime is dissolved in 200 ml of sulpholane and 50 ml of ether, and 19.8 g of pyridine added to the solution. The reaction mixture is stirred overnight at 20°, and the formed suspension filtered. The residue is dried in vacuo at 12 mm Hg and 20° for 16 hours; yield: 33.2 g = 97%; mp. 100°–110°.

EXAMPLE 11

Glyoxime-O,O'-bis-methylcarbonate

2 Parts of chloroformic acid methyl ester are added dropwise at 0° to a solution of 1 part of glyoxime and 2 parts of triethylamine in 5 parts of acetonitrile. After completion of the reaction, the precipitated product is filtered off and the residue stirred with water. A white product, mp. 225° (decomposition), is obtained after filtration and drying.

EXAMPLE 12

Glyoxime-O,O'-bis-N-methylthiocarbamate

2 Parts of melthylisothiocyanate are added to 1 part of glyoxime in 10 parts of acetonitrile. After some time, a spontaneous heating to 40° occurs, whereby the reaction mixture becomes reddish. After a stirring time of several hours, the solvent is evaporated off: a red-brown oil is obtained ($n_D{}^{20}$: 1.595).

EXAMPLE 13

Preparation of zinc-bis-(glyoxime)

2.3 g (0.1 mole) of Na is dissolved in 50 ml of methanol (abs.), and the solution, after completion of the reaction, heated to boiling. With continuous stirring and refluxing, an addition is slowly made dropwise of 6.8 g (0.05 mole) of $ZnCl_2$ in 100 ml of methanol. The solution is cooled and the precipitated sodium chloride filtered in a separating funnel by the solution being pressed with $N_2$ through a glass suction filter. Washing is then performed twice with 20 ml of methanol. A solution of 8.8 g (0.1 mole) of glyoxime in 100 ml of methanol is placed into a flask and, with gentle heating, the solution of Zn ($OCH_3$) added dropwise. The precipitate is filtered off and dried: 2.9 g, Zn content 36.8%, mp. >250°. After standing for 4 hours, the mother liquor is concentrated to ca. 80 ml. Trituration with a spatula is performed and a nicely crystallized substance commences to precipitate. It is filtered, washed and dried; yield: 6.0 g; Zn content: 28.3%, mp. >300°.

EXAMPLE 14

An amount of 2.4 g of magnesium powder is suspended in 50 ml of absolute methanol, and the suspension stirred until no further hydrogen is liberated. An addition is then made dropwise of 8.8 g of glyoxime in 100 ml of methanol. After 30 minutes, the methanol is evaporated off in vacuo. Residue 11.0 g of magnesium glyoximate, mp. >220°.

The preparation of the calcium salt and aluminium salt, respectively, is effected by the same procedure, with calcium hydride or aluminium being used instead of magnesium.

| Compound No. | Formula | physical constants $bp_x$ = boiling point° C. at x Torr mp. = melting point |
|---|---|---|
| 1 | $CH_3(CH_2)_3C(CH_3)=NOH$ | $bp_{11}$: 65° |
| 2 | $(CH_3)_3CC(CH_3)=N-OH$ | mp. 75° |
| 3 | $C_{10}H_{21}C(CH_3)=N-OH$ | mp. 43° |
| 4 | $C_{13}H_{27}C(C_2H_5)=N-OH$ | mp. 40° |
| 5 | $C_5H_{11}-CH=N-OH$ | mp. 51° |
| 6 | $(CH_3)_2C=N-OH$ | mp. 61° |
| 7 | $C_2H_5(CH_3)C=NOH$ | bp. 25 70–78° |
| 8 | $(CH_3)_2C=N-OCOCH_2CH_2-COOH$ | |
| 9 | $[CH_2=N-OH \cdot HCl]$ | mp. 136° (decomp.) |
| 10 | $CH_3-CH=N-OH$ | bp. 113–115° |
| 11 | $(CH_3)_2C-C\overset{N-OH}{\underset{H}{\diagdown}}$ (cyclohexyl) | mp. 174° |
| 12 | $C_2H_5-\underset{\underset{CH_3}{\mid}}{C}=N-O-CO-O-CH_2-CH_2-Cl$ | |
| 13 | $(n-C_4H_9)_2C=N-OH$ | bp. 15 125° |
| 14 | $(n-C_{17}H_{35})_2C=N-OH$ | mp. 65–66° |
| 15 | $(CH_3)_3C-C(n-C_3H_7)=N-OH$ | mp. 58° |
| 16 | $(CH_2)_{11}C=N-OH$ (ring) | mp. 135° |
| 17 | $[(CH_2)_4C=N-OH]$ (ring) | mp. 56–58° |
| 18 | $[(CH_2)_5C=N-OH]$ (ring) | mp. 90° |
| 19 | norbornyl =N-OH  d,l | mp. 118° |
| 20 | $[CH_3CH=CH-CH=N-OH]$ | $bp._{12}$ 65° |
| 21 | $[CCl_3-CH=N-OH]$ | $bp._{12}$: 74° |
| 22 | $[\text{Ph}-CH_2-CH=N-OH]$ | mp. 103° |
| 23 | $[CH_3CO-C(CH_3)-N-OH]$ | mp. 78° |
| 24 | $[CH_3CO-CH=N-OH]$ | mp. 69° |
| 25 | pyridinium-$CH_2-CH=N-OH$ | mp. 110° |
| 26 | $NO_2-CH_2-CH=N-ONa$ (methazonic acid) | mp. 200° (decomp) |
| 27 | $[Cl-CH_2-CH=N-OH]$ | bp. 70° (decomp.) |
| 28 | $C_2H_5OOC-CH=N-OH$ | mp. 53–55° |
| 29 | $[(CH_3)_2N-CH_2-CH=N-OH]$ | bp. 18 105° |
| 30 | $[CH_3-S-CH_2-CH=N-OH]$ | bp. 1 56–58° |
| 31 | $HO-CH_2-CH=N-OH$ | mp. 48–50° (decomp) |
| 32 | $(\text{Ph})_2CH-C(CH_3)=NOH$ | mp. 162° |
| 33 | $HO-N=C(CH_3)-CH(\text{chlorophenyl})(\text{phenyl})$ | mp. 135° |
| 34 | $\text{Ph}-\underset{\underset{O}{\parallel}}{C}-CH=N-OH$ | mp. 126–128° |

-continued

| Compound No. | Formula | physical constants bp_x = boiling point° C. at x Torr mp. = melting point |
|---|---|---|
| 35 | 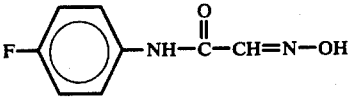 | |
| 36 | 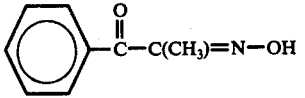 | mp. 113–115° |
| 37 | [HOOC—C(CH₃)=N—OH] | mp. 180° |
| 38 | [NaOOC—C(CH₃)=N—OH] | mp. 340° |
| 39 | HOOC—CH=N—OH | mp. 70° (H₂O), 144° |
| 40 | 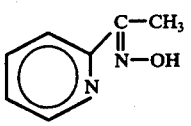 | mp. 122° |
| 41 | 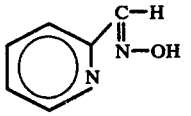 | mp. 109–112° |
| 42 |  | mp. 88–90° |
| 43 | 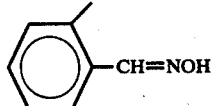 | mp. 130–168° |
| 44 | 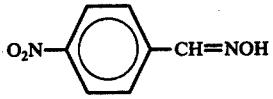 | mp. 129–134° |
| 45 | 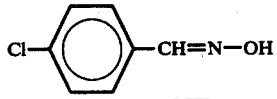 | mp. 110° |
| 46 | 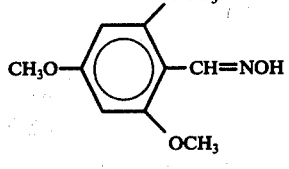 | mp. 213–214° |
| 47 | 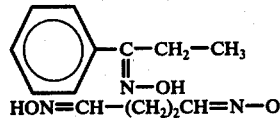 | bp. 100°/ 0.001 Torr |
| 48 | HON=CH—(CH₂)₂CH=N—OH | mp. 152–154° |
| 49 | [HON=C(CH₃)CH₂—C(CH₃)C=N—OH] | mp. 168–170° |
| 50 | [H—O—N=C(Cl)CH=N—OH] | mp. 144° |
| 51 | HO—N=C(Cl)—C(Cl)=NOH | mp. 201° |
| 52 | HO—N=C(CH₃)C(CH₃)=N—OH | mp. 240° |
| 53 | [HON=C(CH₃)—C(Cl)=N—OH] | mp. 187° |
| 54 | [CH₃COON=CH—C(Cl)=N—OCOCH₃] | mp. 91–93° (E,E Isomeres) mp. 118° (E,Z Isomeres) |
| 55 | HON=CH—(CH₂)₃—CH=N—OH | mp. 170–180° |
| 56 | HON=CH—C=NOH<br>           \|<br>          CH₃ | mp. 157° |
| 57 | [CH₃COO—N=CH—CH=N—OCOCH₃] | mp. 125° |
| 58 | CH₃COO—N=CH—CH=N—OH | mp. 120–124° (decom) |
| 59 | [iC₃H₇COON=CH—CH=N—OCOC₃H₇] | mp. 92° |
| 60 | [C₆H₅COON=CH—CH=N—OCOC₆H₅] | mp. 172–176° |
| 61 | [C₁₁H₂₃COON=CH—CH=N—OCOC₁₁H₂₃] | mp. 100–105° |
| 62 | [CH₃NHCOO—N=CH—CH=N—O—CONHCH₃] | mp. 136° |
| 63 | [C₄H₉NHCOO—N=CH—CH=NOCONHC₄H₉] | mp. 112° |
| 64 | CH₃O—N=CH—CH=N—OCH₃ | mp. 215° |

-continued

| Compound No. | Formula | physical constants $bp_x$ = boiling point° C. at x Torr mp. = melting point |
|---|---|---|
| 65 | [C$_6$H$_5$NHCOO—N=CH—CH=N—OCONH—C$_6$H$_5$] | mp. 180° |
| 66 | [pCH$_3$—O—C$_6$H$_4$—COO—N=CH—CH=N—OOC$_6$H$_4$pOCH$_3$] | mp. 200–205° |
| 67 | HO—N=CH—CH=N—OH | mp. 172° |
| 68 | C$_{12}$H$_{25}$—O—N=CH—CH=N—O—C$_{12}$H$_{25}$ | mp. 59° |
| 69 | CH$_2$=CH—CH$_2$—O—N=CH—CH=N—O—CH$_2$—CH=CH$_2$ | mp. 20° |
| 70 | CH$_3$—NH—CO—O—N=CH—CH=N—OH | mp. 40° (Decomp.) |
| 71 | ⌬—CH$_2$—O—N=CH—CH=N—OCH$_2$—⌬ | mp. 72° |
| 72 | CH$_3$—COON=CH—CH=N—OCONHCH$_3$ | |
| 73 | CH$_3$COO—N=CH—CH=N—OCONH—C$_6$H$_5$ | mp. 138 |
| 74 | C$_2$H$_5$OCOO—N=CH—CH=N—OCOOC$_2$H$_5$ | mp. 164° |
| 75 | (CH$_3$)$_2$CH—CH$_2$OCOO—N=CH—CH=N—OCOO—CH$_2$—CH(CH$_3$)$_2$ | mp. 94° |
| 76 | ⌬—CH$_2$—O—COO—N=CH—CH=N—OCOOCH$_2$—⌬ | |
| 77 | ⌬—O—COO—N=CH—CH=N—OCOO—⌬ | |
| 78 | CH$_3$O—CH$_2$CH$_2$—OCOON=CH—CH=N—OCOOCH$_2$CH$_2$—OCH$_3$ | |
| 79 | Br—CH$_2$CH$_2$OCOON=CH—CH=N—OCOOCH$_2$CH$_2$—Br | |
| 80 | CH$_2$=CH—CH$_2$—OCOO—N=CH—CH=N—OCOOCH$_2$—CH=CH$_2$ | |
| 81 | CH$_3$OCOON=CH—CH=N—O—COOCH$_3$ | mp. 226° |
| 82 | (CH$_3$)$_2$NCOO—N=CH—CH=N—OCON(CH$_3$)$_2$ | mp. 134° |
| 83 | C$_2$H$_5$SCOO—N=CH—CH=NOCO—SC$_2$H$_5$ | red oil |
| 84 | ⌬—S—COON=CH—CH=NOOC—S—⌬ | |
| 85 | ⌬O—O—N=CH—CH=N—O—O⌬ (tetrahydropyranyl) | $n_D^{20}$ = 1,504 |
| 86 | CH$_3$NHCS—O—N=CH—CH=N—OSSNHCH$_3$ | $n_D^{20}$ = 1,595 |
| 87 | { HO—N=CH—CH=N—OH, Fe salt } | mp. > 260° |
| 88 | Zn salt | mp. > 260° |
| 89 | Mn salt | mp. > 260° |
| 90 | Co salt | mp. > 260° |
| 91 | Cu salt | mp. > 260° |
| 92 | Na$_2$ salt | mp. > 250° |
| 93 | ethanolamine-salt | viscous oil |
| 94 | Ca salt | mp. 250° |
| 95 | Mg salt | mp. 250° |
| 96 | Al salt | mp.250° |
| 97 | ⌬—CH(OH)—C(=NOH)—⌬ | mp. 153–155° |
| 98 | furyl—C(=NOH)—C(=NOH)—furyl | mp.166–169° |
| 99 | C$_2$H$_5$C(CH$_3$)=N—C(=O)—NH—CH$_2$—CH$_2$Cl | |
| 100 | o-(COOH)C$_6$H$_4$—CH=N—O—C(=O)—O—CH$_2$CH$_2$Cl | |

The active substances of formula I are not phytotoxic in the usual application concentrations, and they have low toxicity towards warm-blooded animals. They moreover produce no morphological changes of the plants or cause damage to them.

They promote, in particular, the developement of abscission layers, particularly between stalks and petioles. Consequently, fruits of all kinds, e.g. stone fruit (cherries), berries, grape vines, pomaceous fruit (apples) or oil fruits (olives), and particularly citrus fruits such as oranges, lemons, grapefruit, etc., can be separated from the fruit stems, manually or mechanically, without any great amount of force being applied. Damage to foliage and branches which normally occurs when fruit is removed by the shaking of trees and shrubs, or by the plucking of the fruit from the branches, is largely avoided, and the production capacity of the trees thus increased.

The extent and nature of the action are governed by the most diverse factors, depending on the type of plant, particularly, however, on the applied concentration and on the time of application with regard to the stage of development of the plant and the fruit. Thus, for example, plants of which the fruit is to be sold, or in some other way utilized, are treated immediately after blossoming or at an appropriate length of time before the gathering of the fruit. The active substances are applied preferably in the form of liquid preparations, these being applied to parts of plants above the soil, to the surface of the soil or into the soil. Application to parts of plants above the soil is preferred, for which purpose solutions or aqueous dispersions are most suitable.

The active substances of formula I are used together with suitable carriers, solvents and/or other additives. Suitable carriers and additives can be solid or liquid, and correspond to the substances normally used in formulation practice, such as, e.g. natural or regenerated mineral substances, solvents, dispersing agents, wetting agents, adhesives and thickening or bonding agents.

The applied amounts are largely governed by the purpose and nature of the application (treatment of the soil or of parts of plants). The usual amounts applied in the case of soil treatment and for crops are between 0.1 and 16 kg. and preferably 1 to 4 kg., or active substance per hectare of land under cultivation.

The agents for promoting abscission which contain active substances of formula I can be formulated as aqueous or non-aqueous solutions and dispersions, emulsifiable concentrates, wetting powders or dusts, optionally with additional amounts of antioxidants such as hydroquinone. Such formulations can contain 2 to 95 percent by weight, preferably 80 to 90 percent by weight, of active substance, and can be prepared by the techniques normally applied in agricultural chemistry. Preferred preparations are aqueous ones having a content of 0.1 to 1% of a nonionic wetting agent. The time of application to promote fruit abscission is shortly before harvesting, i.e. 3 days to 4 weeks before harvesting.

EXAMPLE 15

The determination of the abscission action on citrus plants was made by the following methods:

A. On freshly sprouted branches of *Citrus sinensis* var. Volkameriana, the leaf surface was cut off from 8 leaves, leaving only the leaf-stalks on the branch. Two such branches in each case were then sprayed with active-substance content, respectively. The test was evaluated after 7 days on the basis of the number of shed leaf-stalks. In all the control tests, no leaf-stalk was shed.

B. Parts of branches of orange trees (variety Hamlin or Pineapple or Valencia) carrying at least 20 oranges were sprayed with active-substance solutions shortly before harvesting. The evaluation of the test results was made after 7 days, with two different systems being employed:

a. *Measurement of the plucking force* and determination of the reduction thereof effected, with respect to the untreated control specimens.

b. *Number of shed oranges* (without shaking) in percent, compared with the untreated control specimens (0%).

All active substances tested produced, with no or negligible shedding of leaves, an intense development of abscission layers on the fruit-stalks, an appreciable reduction of plucking force, and some of them even good values with regard to the shedding of fruit.

Especially good results have so far been obtained with compounds Nos. 7, 8, 17, 23, 24, 32, 42, 48, 49, 51, 52, 67, 88, 91, 95, 97 and 98.

In the case of Hamlin oranges with a 4000 ppm concentration of active substance O-(2-chloroethoxycarbonyl)butaneoxime, the plucking forces required after 7 days were less than a quarter of those required for untreated oranges, these being 9 to 11 kg per orange. Similarly good reductions in plucking force were obtained with dichloroglyoxime and glyoxime, as noted in the following table:

|  | Concentration (ppm) | Pull Force (lbs.) | |
|---|---|---|---|
|  |  | Treated | Carrier Treated Control |
| Hamlin Oranges |  |  |  |
| dichloroglyoxime | 2000 | 6.4 | 21.3 |
|  | 4000 | 6.0 | 21.3 |
| Valencia Oranges |  |  |  |
| glyoxime | 500 | 0* | 18.2 |
|  | 1000 | 0* | 18.2 |
| Grapefruits |  |  |  |
| glyoxime | 250 | 14.9 | 16.4 |
|  | 500 | 10.2 | 16.4 |
|  | 750 | 8.9 | 16.4 |
| Cherries |  |  |  |
| glyoxime | 1000 | 606.5 grams | 663.8 grams |
| Apples |  |  |  |
| glyoxime | 2000 | 5.0 | 5.5 |
|  | 4000 | 4.1 | 5.5 |
| Prunes |  |  |  |
| glyoxime | 2000 | 2.4 | 4.1 |

*substantially total fruit drop

Other test procedures included:

*Walnut Huskability* — Walnut branches were sprayed with the indicated concentrations of active material shortly before harvesting. Evaluation of the test results (20 walnuts) was made after seven days utilizing the following rating system 1 = husk split on tree
2 = husk split by finger pressure
3 = husk split by prying with knife
4 = ¼ husk tightly adhered

|  |  | Husk Rating | |
|---|---|---|---|
|  |  | Treated | Control |
| glyoxime | 500 ppm | 1.4 | 1.7 |
|  | 1000 ppm | 1.2 | 1.7 |
|  | 2000 ppm | 1.3 | 1.7 |

*Olive Fruit Drop* — Olive branches were sprayed with the indicated concentrations of active material shortly before harvesting. Evaluation of the test results was made after seven days by determining the amount of unassisted mature fruit drop

| glyoxime | | % Fruit Drop | |
|---|---|---|---|
| | | Treated | Control |
| glyoxime | 500 ppm | 2.3 | 2.0 |
| | 1000 ppm | 5.5 | 2.0 |
| | 2000 ppm | 8.8 | 2.0 |
| | 4000 ppm | 17.5 | 2.0 |

*Grape Drop* — Grape vines were sprayed with 4000 ppm of glyoxime solutions shortly before harvest. Representative bunches were then subjected to vibration for a period of 15 seconds whereupon % fruit removal was noted. In this test, the glyoxime treated sample exhibited 72% removal as contrasted with 59.6% for the untreated grapes.

EXAMPLE 16

The abscission test described in Example 15, hereinabove, was repeated under identical conditions utilizing glyoxime and phenylglyoxime as the active substances. The active substances were prepared, in a concentration of 1000 ppm, as an aqueous liquor. Each test was conducted by spraying the solution on branches of Hamlin orange trees and evaluating the results after a seven day period.

In this test, the phenylglyoxime exhibited virtually no activity as regards reducing the pull force or effecting mature fruit drop as contrasted with the glyoxime which exhibited a 100% mature fruit drop in combination with a preferred 0% mature leaf drop. These test results thus indicate the inapplicability of phenylglyoxime as an abscission agent in accordance with this invention.

I claim:

1. A process of aiding in the harvesting of fruit particularly for the promotion of the facilitation of fruit adscission, which process comprises applying to the fruit-bearing plant or to the fruit itself an effective amount of an oxime compound selected from the group consisting of glyoxime, dichloroglyoxime and the alkali metal, alkaline-earth metal, copper and aluminum salts thereof.

2. The process according to claim 1, wherein said active substance is glyoxime.

3. The process according to claim 1, wherein said fruit is citrus fruit.

* * * * *